(12) United States Patent
Ruhle

(10) Patent No.: US 10,188,785 B1
(45) Date of Patent: Jan. 29, 2019

(54) VAGINAL CLEANSING DEVICE

(71) Applicant: Sharon Ruhle, Cranston, RI (US)

(72) Inventor: Sharon Ruhle, Cranston, RI (US)

( * ) Notice: Subject to any disclaimer, the term of this patent is extended or adjusted under 35 U.S.C. 154(b) by 267 days.

(21) Appl. No.: 15/270,119

(22) Filed: Sep. 20, 2016

(51) Int. Cl.
*A61M 3/00* (2006.01)

(52) U.S. Cl.
CPC ....... *A61M 3/00* (2013.01); *A61M 2210/1475* (2013.01)

(58) Field of Classification Search
CPC .. A61M 3/00; A61M 2210/1475; A61M 3/02; A61M 35/00; A61M 35/003; A61M 35/006
USPC ......................................................... 604/1–3
See application file for complete search history.

(56) References Cited

U.S. PATENT DOCUMENTS

| | | | |
|---|---|---|---|
| 2,881,760 A | 4/1959 | Mcgiveran | |
| 3,228,398 A * | 1/1966 | Leonard ................ | A61F 13/266 15/244.1 |
| 3,640,268 A * | 2/1972 | Davis ..................... | A61B 10/02 401/119 |
| 3,709,224 A * | 1/1973 | Fielding .............. | A61M 3/0279 604/2 |
| 3,818,911 A * | 6/1974 | Fournier ................. | A61F 13/38 15/244.2 |
| 4,260,570 A * | 4/1981 | Ravel ..................... | A61B 17/42 264/46.6 |
| 4,309,995 A | 1/1982 | Sacco | |
| 4,329,990 A | 5/1982 | Sneider | |
| D319,699 S | 9/1991 | Dunning | |
| 6,379,341 B1 | 4/2002 | Cho | |
| 7,112,184 B2 * | 9/2006 | Bichsel ............... | A61F 13/2051 604/1 |
| 7,311,688 B2 * | 12/2007 | Bichsel ............... | A61F 13/2051 604/15 |
| 7,507,223 B2 | 3/2009 | Fontana | |
| 8,007,478 B2 | 8/2011 | Lu | |
| 2005/0187507 A1 | 8/2005 | Reed | |
| 2006/0069338 A1 * | 3/2006 | Bichsel ............... | A61F 13/2051 604/2 |
| 2006/0069342 A1 * | 3/2006 | Bichsel ............... | A61F 13/2051 604/14 |
| 2006/0264851 A1 | 11/2006 | Coleman | |
| 2007/0156077 A1 * | 7/2007 | Pfister ................. | A61M 35/006 604/2 |
| 2014/0276429 A1 * | 9/2014 | Shin ....................... | A61M 3/02 604/151 |

FOREIGN PATENT DOCUMENTS

WO    2012022995 A1    2/2012

\* cited by examiner

*Primary Examiner* — Susan S Su

(57) ABSTRACT

The vaginal cleaning device is a lavage device that is adapted for use in personal hygiene. The lavage device is designed to reduce the risk of irritation caused by the inappropriate handling of the lavage device. This is done by eliminating the need to physically handle the dressing associated with the lavage device. The dressing is a sterile absorbent dressing that is contained within a sterile container. The dressing is removed from the sterile container using a plug and port arrangement that inserts an assumedly non-sterile plug into a port that is formed in the center of the dressing. This arrangement separates by distance the non-sterile plug from the sterile surface of the dressing. The lavage device comprises a handle, a dressing, and a sterile container.

6 Claims, 4 Drawing Sheets

US 10,188,785 B1

VAGINAL CLEANSING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of medical and hygiene, more specifically, an absorbent dressing adapted for internal application to the body.

Lavage devices adapted for use in the personal hygiene are known as a common source for vaginal infections. These infections are a result of the practical difficulties in appropriately handling such lavage devices in a manner that avoids the cross contaminations that result in such infections.

Clearly, a lavage device that simplifies personal cleansing while reducing the risks of cross contamination would be of benefit.

SUMMARY OF INVENTION

This disclosure addresses the shortcomings described above.

The vaginal cleaning device is a lavage device that is designed to reduce the risk of irritation caused by the inappropriate handling of the lavage device. This is done via eliminating the need to physically handle the dressing associated with the lavage device. The dressing is a sterile absorbent dressing that is contained within a sterile container. The dressing is removed from the sterile container using a plug and port arrangement that inserts an assumedly non-sterile plug into a port that is formed in the center of the dressing. This arrangement separates by distance the non-sterile plug from the sterile surface of the dressing. In a described potential embodiment of the disclosure, the dressing is further treated before packaging to improve the cleansing effectiveness. In a described alternate embodiment of the disclosure, the port is treated with an antiseptic to further decrease the risks of cross contamination.

These together with additional objects, features and advantages of the vaginal cleaning device will be readily apparent to those of ordinary skill in the art upon reading the following detailed description of the presently preferred, but nonetheless illustrative, embodiments when taken in conjunction with the accompanying drawings.

In this respect, before explaining the current embodiments of the vaginal cleaning device in detail, it is to be understood that the vaginal cleaning device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the vaginal cleaning device.

It is therefore important that the claims be regarded as including such equivalent construction insofar as they do not depart from the spirit and scope of the vaginal cleaning device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summery or the following detailed description.

Figure 1:
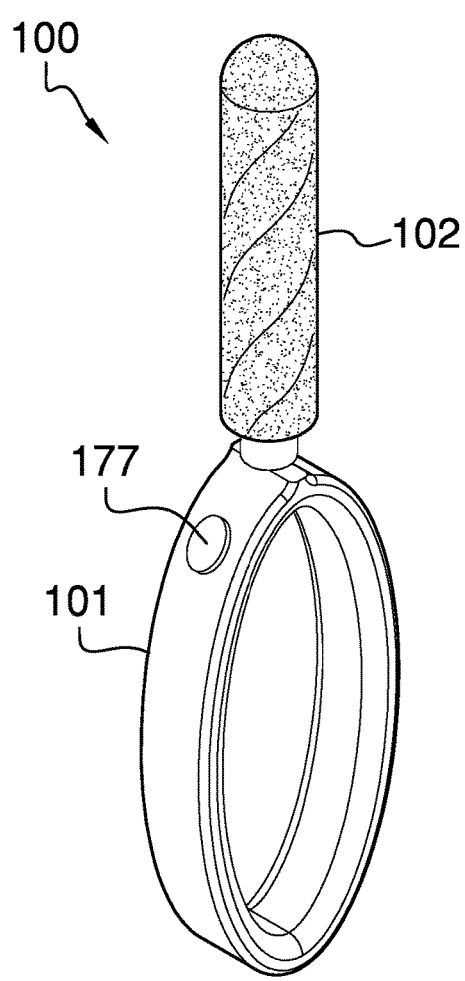
FIG. 1 is a perspective view of an embodiment of the disclosure.
Figure 2:
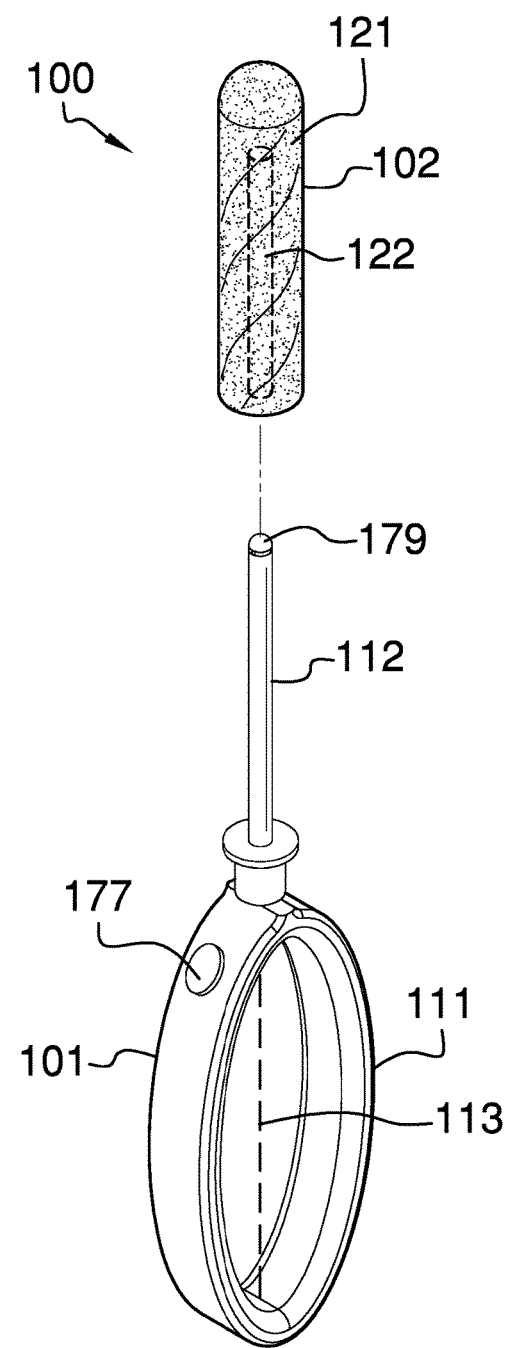
FIG. 2 is an exploded view of an embodiment of the disclosure.
Figure 3:
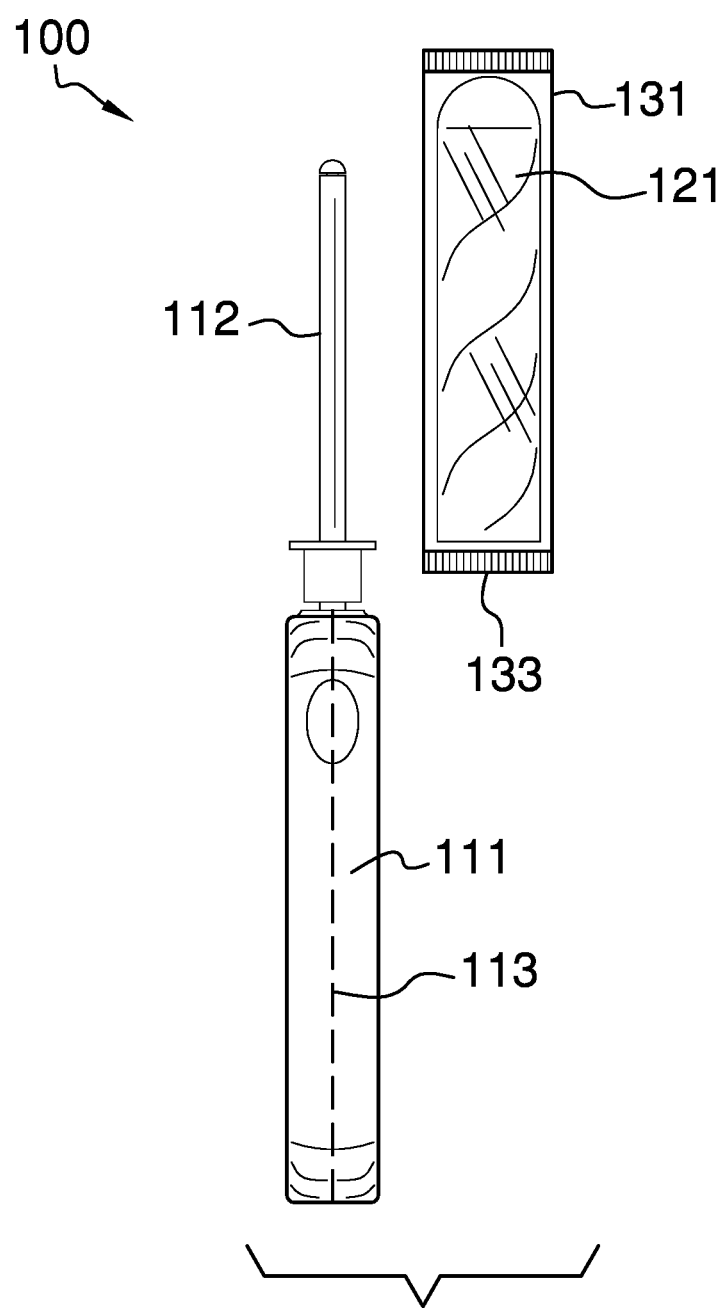
FIG. 3 is a side view of an embodiment of the disclosure.
Figure 4:
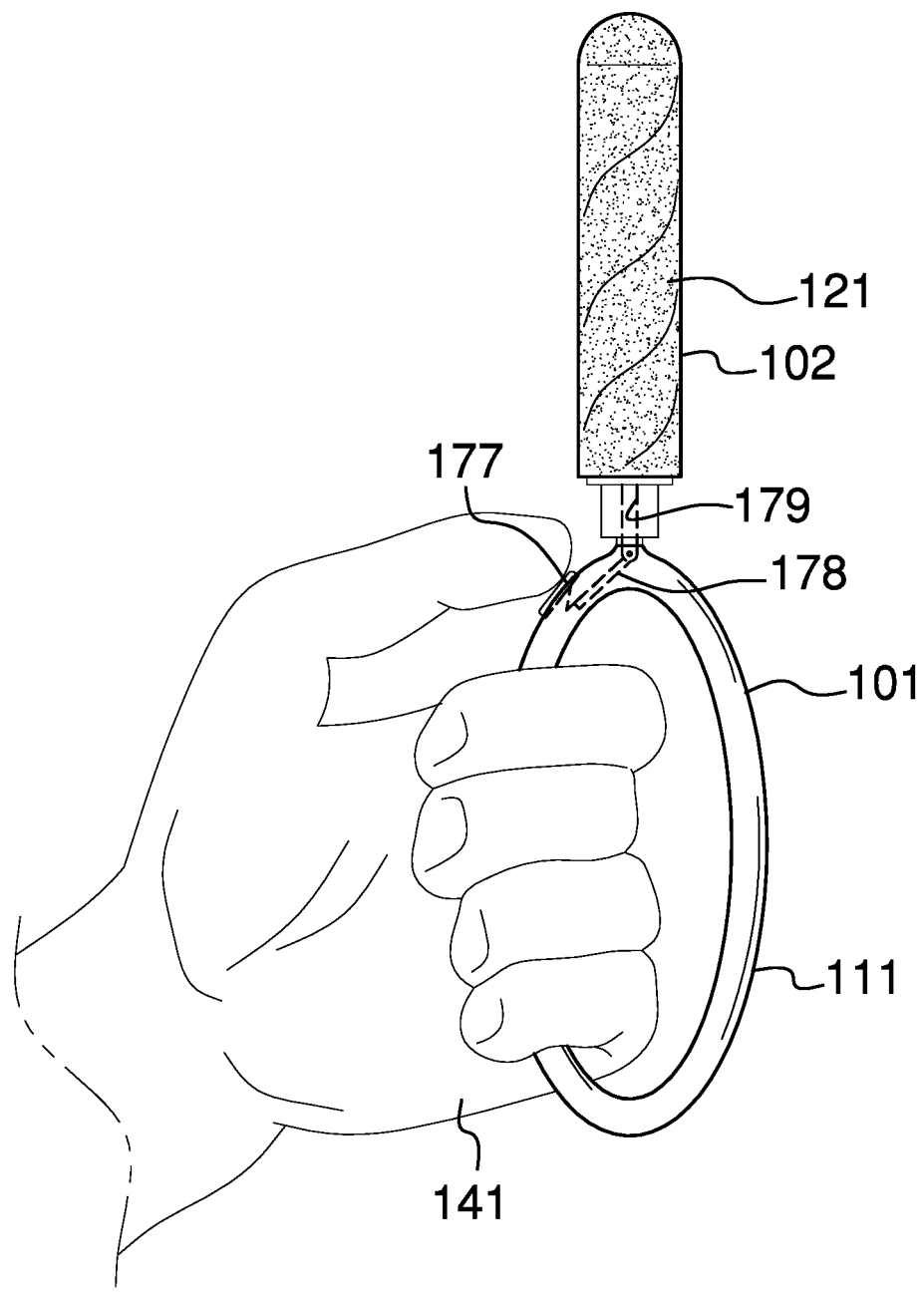
FIG. 4 is a front view of an embodiment of the disclosure.
Figure 5:
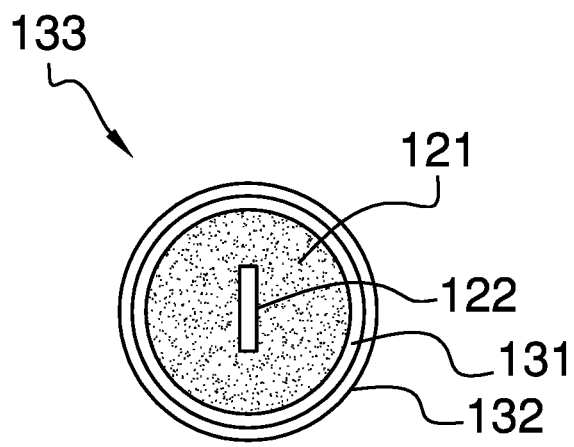
FIG. 5 is a detail view of an embodiment of the disclosure.

Detailed reference will now be made to one or more potential embodiments of the disclosure, which are illustrated in FIGS. 1 through 5.

The vaginal cleaning device 100 (hereinafter lavage device) comprises a handle 101, a dressing 102, and a sterile container 103. The lavage device 100 is adapted for use in personal hygiene. The lavage device 100 is adapted for use in cleaning a body cavity. The lavage device 100 is designed to reduce the risk of irritation caused by the inappropriate handling of the lavage device 100. This is done by eliminating the need to physically touch the dressing 102 associated with the lavage device 100. The dressing 102 is a sterile absorbent dressing 102 that is contained within a sterile container 103. The dressing 102 is removed from the sterile container 103 using a plug 112 and port 122 arrangement that inserts an assumedly non-sterile plug 112 into a port 122 that is formed in the center of the dressing 102. This arrangement separates by distance the non-sterile plug 112 from the sterile surface of the dressing 102. In a described potential embodiment of the disclosure, the dressing 102 is previously treated before packaging to improve the cleansing effectiveness of the lavage device 100. In a described alternate embodiment of the disclosure, the port 122 is treated with an antiseptic to further decrease the risks of cross contamination.

The handle 101 comprises a grip 111 and a plug 112. As shown most clearly in FIG. 2, the grip 111 is an oval ring that is grasped by the hand 141 to manipulate the lavage device 100. The plug 112 is a cylindrical shaft that projects away from the grip 111 along the major axis 113 of the oval in a direction away from the focal point of the oval. The plug 112 is further defined with an outer diameter.

The dressing 102 comprises a textile 121 and a port 122. The textile 121 is a commercially available textile that is used to form a soft, sponge like and absorbent mass that will be used to clean the body cavity. The textile 121 is designed to be elastic for purposes described elsewhere within this disclosure. As shown most clearly in FIG. 2, the textile 121 is formed roughly in a cylindrical shape. The port 122 is a cylindrically shaped cavity that is formed along the center axis of the textile 121. The port 122 is further defined with an inner diameter. In the textile's 121 relaxed shape, the span of the inner diameter of the port 122 is less than the span of the outer diameter of the plug 112. This mismatch between the plug 112 and the port 122 causes the textile 121 around the port 122 to expand when the plug 112 is inserted into the port 122. As the textile 121 attempts to return to its relaxed shape, a force is applied by the textile 121 to the plug 112 which has the effect of holding the textile 121 in position during use of the lavage device 100. The dressing is intended for single use and is disposed of after use. Methods to form textiles as described within this disclosure are known within the textile arts.

The sterile container 103 comprises a capped tube 131 and a sealing film 132. The capped tube 131 is a tube with a closed end. The capped tube 131 is a gas and fluid impermeable structure that is sterilized before the textile 121 is inserted into the capped tube 131. The capped tube 131 is sized such that the textile 121 has to be compressed to fit properly within the capped tube 131. The forces applied by the textile 121 as it tries to return to its relaxed shape will assist in removing the textile 121 from the capped tube 131 in preparation for use. As shown most clearly in FIG. 5, the textile 121 is inserted into the capped tube 131 such that the port 122 is accessible from the open end 133 of the capped tube 131. This allows the plug 112 to be inserted into the port 122 to remove the textile 121 from the capped tube 131. The capped tube 131 is sealed with the sealing film 132 thus ensuring the sterility of the textile 121 until use. The sealing film 132 is a commercially available gas and fluid impermeable plastic sheeting. Methods to insert and seal a sterile dressing 102 within a sterile container 103 are well known and documented within the medical arts.

To use a first potential embodiment of the disclosure as described above, the plug 112 of the handle 101 is pressed through the sealing film 132 and directly into the port 122 of the textile 121. The textile 121 is then removed from the capped tube 131 without further handling requirements. Depending on the design, the sealing film 132 may be designed to be removed with the dressing 102 or may be designed to tear away and remain with the sterile container 103 as the textile 121 is removed.

In a second potential embodiment of the disclosure, the textile 121 is treated with a cleansing solution comprising sterilized water and acetic acid before the textile 121 is packaged within the sterile container 103. The previously moistened textile 121 is then packaged within the sterile container 103 as previously discussed in this disclosure.

In a third potential embodiment of the disclosure, the textile 121 is chemically treated with a more aggressive pharmacologically active treatment before the textile 121 is packaged within the sterile container 103. The more aggressive previous treatment of the textile 121 comprises one or more chemicals adapted for use in antiseptic treatments or antifungal treatments. Depending on the goal the previous treatment may be with a single chemical or a combination of chemicals. Suitable pharmacologically active treatment for use in previously treatment include, but are not limited to, a selection of one or more of the following chemicals: 2-pyrrolidinone with iodine, ((2-chlorophenyl)-diphenylmethyl) imidazole, undec-10-enoic acid, or (RS)-1-(2-(2,4-dichlorobenzyloxy)-2-(2,4-dichlorophenyl)ethyl)-1H-imidazole. Optimally these chemicals may be applied as a gel or powder to the textile 121. In this state, the natural moisture of the body will be used to distribute the pharmacologically active treatment during cleansing. The more aggressively treated textile 121 is then packaged within the sterile container 103 as previously discussed.

In a fourth potential embodiment of the disclosure, the port 122 is filled with a gel containing 2-pyrrolidinone with iodine to further sanitize the plug 112 when it is inserted into the port 122. Methods to make gels containing 2-pyrrolidinone with iodine are known and documented in the medical arts. The treated textile 121 with this treated port 122 is then packaged within the sterile container 103 as previously discussed.

In the first potential embodiment of the disclosure, the handle 101 is formed as a single unit from polycarbonate. The dressing 102 is a commercially available combination of cotton and polyester fibers. The sterile container 103 is formed from plastic and sealed with a plastic sheeting.

The handle 101 may include a spring-loaded button 177, which when depressed shall release the dressing 102. The spring-loaded button 177 is positioned on the handle 101 in a locale that the hand 141 is easily accessible to, and which enables ease of depression. Upon depression of the spring-loaded button 177, the dressing 102 becomes released from the plug 112 in order for the dressing 102 to be discarded after use. Moreover, the spring-loaded button 177 is in connection with a linkage 178 that moves within the handle 101. The linkage 178 in turn moves a tip member 179 in order to drive the dressing 102 upwardly from the plug 112. The tip member 179 is in telescopic arrangement with the plug 112 such that the tip member 179 extends down the plug 112 to where the tip member 179 interfaces with the linkage 178 (see FIG. 4).

The following definitions were used in this disclosure:

(RS)-1-(2-(2,4-dichlorobenzyloxy)-2-(2,4-dichlorophenyl)ethyl)-1H-imidazole: As used in this disclosure, (RS)-1-(2-(2,4-dichlorobenzyloxy)-2-(2,4-dichlorophenyl)ethyl)-1H-imidazole is an antifungal chemical substance commonly referred miconazole.

2-chlorophenyl)-diphenylmethyl) imidazole: As used in this disclosure, 1-((2-chlorophenyl)-diphenylmethyl) imidazole is an antifungal chemical substance commonly referred to a chlotrimazole.

2-pyrrolidinone with iodine: As used in this disclosure, 2-pyrrolidinone with iodine is an antiseptic chemical substance commonly referred to a povidone iodine.

Capped Tube: As used in this disclosure, a capped tube is a tube with one closed end and one open end.

Elastic: As used in this disclosure, an elastic is a material or object that deforms when a force is applied to it and that is able to return to its original shape after the force is removed. A material that exhibits these qualities is also referred to as an elastomeric material.

Fiber: As used in this disclosure, a fiber is a slender elongated structure.

Inner Diameter: As used in this disclosure, the term inner diameter is used in the same way that a plumber would refer to the inner diameter of a pipe.

Lavage: As used in this disclosure, lavage refers to the cleansing of a body cavity.

Outer Diameter: As used in this disclosure, the term outer diameter is used in the same way that a plumber would refer to the outer diameter of a pipe.

Relaxed Shape: As used in this disclosure, a structure is considered to be in its relaxed state when no shear, strain, or torsional forces are being applied to the structure.

Sheeting: As used in this disclosure, sheeting is a material, such as cloth or plastic, in the form of a thin flexible layer or layers.

Textile: As used in hit, disclosure, a textile is a material that is woven, knitted, braided or felted. Synonyms in common usage for this definition include fabric and cloth.

Tube: As used in this disclosure, a tube is a hollow cylindrical device with a first open end and a second open end that is used for transporting liquids and gasses.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A lavage device comprising:
a handle, a dressing, and a sterile container;
wherein the lavage device is adapted for use in personal hygiene;
wherein the lavage device is adapted for use with a body cavity;
wherein the dressing is a sterile absorbent dressing that is contained within the sterile container;
wherein the dressing is removed from the sterile container using the handle;
wherein the lavage device separates by distance the non-sterile handle from the sterile surface of the dressing;
wherein the handle comprises a grip and a plug;
wherein the grip is a ring;
wherein the plug is a cylindrical shaft that projects away from the grip;
wherein the plug is further defined with an outer diameter;
wherein the dressing comprises a textile and a port;
wherein the textile is elastic;
wherein the port is a cylindrically shaped cavity that is formed along the center axis of the textile;
wherein the port is further defined with a diameter;
wherein the span of the diameter of the port is less than the span of the outer diameter of the plug when the textile is in a relaxed state;
wherein the plug inserts into the port;
wherein the textile expands when the plug is inserted into the port such that when the textile returns to its relaxed shape a force is applied by the textile to the plug;
wherein the dressing is disposable;
wherein the sterile container comprises a capped tube and a sealing film;
wherein the sealing film attaches to the capped tube
wherein the capped tube is a gas and fluid impermeable structure;
wherein the capped tube is further defined with an open end;
wherein the capped tube is sterilized;
wherein the textile is inserted into the capped tube;
wherein the textile compresses when inserted into the capped tube;
wherein the open end of the capped tube is sealed with the sealing film;
wherein the sealing film is a plastic sheeting;
wherein the plug of the handle is pressed through the sealing film and directly into the port of the textile.

2. The lavage device according to claim 1 wherein the textile is treated with a cleansing solution comprising sterilized water and acetic acid.

3. The lavage device according to claim 1 wherein the textile is chemically treated with a pharmacologically active treatment.

4. The lavage device according to claim 3 wherein the pharmacologically active treatment comprises one or more chemical substances selected from the group of chemical substances consisting of 2-pyrrolidinone with iodine, 1-((2-chlorophenyl)-diphenylmethyl) imidazole, undec-10-enoic acid, or (RS)-1-(2-(2,4-dichlorobenzyloxy)-2-(2,4-dichlorophenyl)ethyl)-1H-imidazole.

5. The lavage device according to claim 1 wherein the port is filled with a gel containing 2-pyrrolidinone with iodine.

6. The lavage device according to claim 1 wherein the handle includes a spring-loaded button, which when depressed shall release the dressing; wherein the spring-loaded button is positioned on the handle in a locale that the hand is easily accessible to, and which enables ease of depression; wherein upon depression of the spring-loaded button, the dressing becomes released from the plug in order for the dressing to be discarded after use; wherein the spring-loaded button is in connection with a linkage that moves within the handle; wherein the linkage in turn moves a tip member in order to drive the dressing upwardly from the plug; wherein the tip member is in telescopic arrangement with the plug such that the tip member extends down the plug to where the tip member interfaces with the linkage.

* * * * *